(12) United States Patent
McElroy et al.

(10) Patent No.: US 10,888,670 B2
(45) Date of Patent: Jan. 12, 2021

(54) INTEGRATED PASSIVE SYRINGE NEEDLE SAFETY SYSTEM WITH TORQUED COMPRESSION SPRING AND MULTI-PART COLLAR

(71) Applicant: West Pharmaceutical Services, Inc., Exton, PA (US)

(72) Inventors: Terry McElroy, Bray (IE); Colin Dowling, Dublin (IE); Patrick Dowling, Dublin (IE); Martin McGarry, Dublin (IE)

(73) Assignee: WEST PHARMACEUTICAL SERVICES, INC., Exton, PA (US)

( * ) Notice: Subject to any disclaimer, the term of this patent is extended or adjusted under 35 U.S.C. 154(b) by 0 days.

(21) Appl. No.: 16/637,124

(22) PCT Filed: Aug. 13, 2018

(86) PCT No.: PCT/US2018/046468
§ 371 (c)(1),
(2) Date: Feb. 6, 2020

(87) PCT Pub. No.: WO2019/033092
PCT Pub. Date: Feb. 14, 2019

(65) Prior Publication Data
US 2020/0254194 A1 Aug. 13, 2020

Related U.S. Application Data (60) Provisional application No. 62/544,202, filed on Aug. 11, 2017.

(51) Int. Cl.
*A61M 5/32* (2006.01)

(52) U.S. Cl.
CPC ........ *A61M 5/3271* (2013.01); *A61M 5/3202* (2013.01); *A61M 5/326* (2013.01);
(Continued)

(58) Field of Classification Search
CPC .............. A61M 5/3272; A61M 5/3271; A61M 5/3202; A61M 5/326; A61M 5/3293;
(Continued)

(56) References Cited

U.S. PATENT DOCUMENTS

| 4,644,941 A | 2/1987 | Ogle, II |
| 4,915,697 A * | 4/1990 | DuPont ................. A61M 5/326 604/192 |

(Continued)

FOREIGN PATENT DOCUMENTS

| DE | 102015110343 A1 | 12/2016 |
| FR | 3037807 A1 | 12/2016 |

(Continued)

OTHER PUBLICATIONS

Int'l Search Report and Written Opinion dated Oct. 31, 2018 in Int'l Application No. PCT/US2018/046508.
(Continued)

*Primary Examiner* — Kevin C Sirmons
*Assistant Examiner* — Alexandria Lalonde
(74) *Attorney, Agent, or Firm* — Panitch Schwarze Belisario & Nadel LLP (57) ABSTRACT

A needle safety system for a syringe having a generally cylindrical barrel extending along a longitudinal axis, the barrel having a hub from which a needle extends distally. The needle safety device has a sleeve at least partially enclosing the needle. A guide track is formed in the sleeve. A multi-part collar disposed in the sleeve has an inner collar which is fixedly connectable to the hub of a syringe barrel. An outer collar is rotatably attached to the inner collar. A guide pin extending radially outwardly from the outer collar slideably engages the guide track. A torqueable compression spring extending between the outer collar and the sleeve
(Continued)

biases the sleeve in a distal direction and also biases the outer collar in rotation relative to the sleeve.

21 Claims, 5 Drawing Sheets

(52) U.S. Cl.
CPC ........ *A61M 5/3213* (2013.01); *A61M 5/3272* (2013.01); *A61M 5/3293* (2013.01); *A61M 2005/3267* (2013.01)

(58) Field of Classification Search
CPC ........ A61M 5/3204; A61M 2005/3267; A61M 2005/3256; A61M 2005/3252
See application file for complete search history.

(56) References Cited

U.S. PATENT DOCUMENTS

| | | | |
|---|---|---|---|
| 4,966,592 | A | 10/1990 | Burns et al. |
| 5,536,047 | A | 7/1996 | Detable et al. |
| 10,335,552 | B2 | 7/2019 | Grosser |
| 2007/0256827 | A1 | 11/2007 | Guerrero et al. |
| 2009/0324327 | A1 | 12/2009 | McAndrews et al. |
| 2015/0190586 | A1 | 7/2015 | Takemoto |
| 2015/0246182 | A1 | 9/2015 | Evans et al. |
| 2016/0174960 | A1 | 6/2016 | Albrecht et al. |

FOREIGN PATENT DOCUMENTS

| | | |
|---|---|---|
| WO | 2016091554 A1 | 6/2016 |
| WO | 2016158627 A1 | 10/2016 |
| WO | 2016202498 A1 | 12/2016 |
| WO | 2016202614 A1 | 12/2016 |
| WO | 2016202670 A1 | 12/2016 |
| WO | 2017012833 | 1/2017 |

OTHER PUBLICATIONS

Int'l Preliminary Report on Patentability dated Nov. 11, 2019 in Int'l Application No. PCT/US2018/046508.
Int'l Preliminary Report on Patentability dated Oct. 23, 2019 in Int'l Application No. PCT/US2018/046492.
Int'l Search Report and Written Opinion dated Oct. 27, 2018 in Int'l Application No. PCT/US2018/046492.
Int'l Search Report and Written Opinion dated Nov. 27, 2018 in Int'l Application No. PCT/US2018/046468.
Int'l Preliminary Report on Patentability dated Aug. 28, 2019 in Int'l Application No. PCT/US2018/046468.

\* cited by examiner

INTEGRATED PASSIVE SYRINGE NEEDLE SAFETY SYSTEM WITH TORQUED COMPRESSION SPRING AND MULTI-PART COLLAR

CROSS-REFERENCE TO RELATED APPLICATIONS

This application is a section 371 of International Application No. PCT/US2018/046468, filed Aug. 13, 2018, which was published on Feb. 14, 2019 under International Publication No. WO 2019/033092 A1, and which claims priority to U.S. Provisional Patent Application No. 62/544,202, filed Aug. 11, 2017, each of which is incorporated herein by reference in its entirety.

BACKGROUND

Needlestick injuries are an occupational hazard for healthcare workers. Unintended needlesticks have the potential for transmitting blood-borne viruses such as hepatitis B and C and the human immunodeficiency virus (HIV) to the recipient. After a needlestick injury, certain procedures must be followed to minimize the risk of infection for the recipient, such as laboratory blood tests and post-exposure prophylaxis started immediately after exposure to a pathogen, such as one of the aforementioned viruses, in order to prevent infection by the pathogen and the development of the associated disease.

The risk of needlestick injuries increases when medicines are administered in a non-hospital or medical care facility environment. This is often the case when vaccines and other necessary medicines are administered in the field or in an emergency.

Safety devices have been used to reduce the frequency of post-injection needlesticks. Some safety devices may have a sheath partially or completely surrounding the needle of a syringe, and be operatively coupled to the syringe. The sheath may be held in a retracted position exposing the needle for aspiration and injection and may be automatically deployed around a needle afterwards. A needle safety device which malfunctions can increase the risk of needlesticks. It is critical that a needle safety device work every time.

The hub, shoulder and cone area of the syringe, the area between the hub and shoulder area of the main barrel typically varies dimensionally due to manufacturing process variability. And the variability of the hub, shoulder and cone area can vary depending upon the type of syringe and the specific material used to make the syringe. These areas tend to vary more for glass syringes than for some plastic syringes. The syringe hub, shoulder and cone area geometry can also vary batch to batch and among syringe manufacturers. Consequently, a needle safety device which is operatively coupled to the syringe in the hub, shoulder and cone area of the syringe can bind or malfunction due to the variability of the dimensions of the hub, shoulder and cone area.

BRIEF SUMMARY

In an exemplary embodiment, a needle safety system for a syringe is disclosed. The needle safety system may include a sleeve, within which a barrel of a syringe is moveable, at least partially enclosing the needle, a guide track formed in the sleeve, and a collar disposed in the sleeve. The collar may have an inner collar portion fixedly attachable to a hub of a syringe and an outer collar portion rotatably attached to the inner collar portion and having a guide pin extending radially from the outer collar portion. In the safety system, the guide pin slides within the guide track, and a spring extends between the outer collar portion and the sleeve. Further, the spring biases the sleeve in a distal direction and also biases the outer collar portion in rotation relative to the sleeve.

In some embodiments of the needle safety system the inner collar portion includes a generally cylindrically-shaped base with an inner-collar bore therethrough; a distal end of the inner-collar base forming a radially outwardly-extending, distally-facing annular surface; a plurality of radially-disposed, circumferentially-spaced deflectable members protruding distally from the annular surface, each deflectable member sufficiently compliant to allow passage of a distal end of a hub of a syringe through the inner-collar bore and to fixedly attach the inner collar portion to a radially outwardly facing distal-hub surface of a syringe by a radially inwardly-directed force applied by each flexible finger to a radially outwardly-facing distal-hub surface of a syringe; and a plurality of radially-disposed, circumferentially-spaced-apart legs protruding proximally, and a distal end of each deflectable member abuts a proximally-facing distal-hub annular shoulder of a syringe and a proximal end of each circumferentially-spaced-apart leg abuts a barrel shoulder of a syringe when the inner collar portion is fixedly attached to a hub of a syringe.

In some embodiments of the needle safety system, at least one cut-out is provided between the circumferentially-spaced-apart legs allowing inspection of contents inside a barrel of a syringe.

In some embodiments of the needle safety system, an opposed radially inwardly-facing surface of the distal end of each deflectable member has a taper corresponding to a radially outwardly-facing distal-hub surface of a syringe.

In some embodiments of the needle safety system, the outer collar portion has an outer collar bore with a radially inwardly-extending outer collar ring and a channel formed in the distal end of each deflectable member collectively forms a circular channel in the radially outwardly-facing surface of the inner collar portion, the circular channel configured to receive and retain freely rotatable therein the radially inwardly-extending outer collar ring.

In some embodiments of the needle safety system, the outer collar portion is sufficiently compliant and sized to allow passage of the deflectable members through the outer collar bore, and insertion of the outer collar ring in the circular channel and to return to an initial outer collar configuration in which the outer collar portion is freely rotatable, preferably, in only one degree of freedom relative to the inner collar portion.

In some embodiments of the needle safety system, the guide track has a first track segment beginning with a first catch, and a second track segment contiguous with the first track segment and ending with a second catch, and when the inner collar portion is attached to a hub of a syringe, and the guide pin is positioned in the first catch, the needle safety system is in a pre-injection position, when the guide pin is moved out of the first catch to the distal end of the first track segment, the needle safety system is in a full-insertion position exposing a needle of a syringe, and when the guide pin is moved along the second track segment to the second catch a needle of a syringe is entirely enclosed in the sleeve and the guide pin is locked therein by the rotational bias of the spring toward the second catch.

In some embodiments of the needle safety system, a spring may be used which has a distal end with a distally extending leg disposed in a sleeve receptacle in the distal end of the sleeve and a proximal end with a proximally extending leg disposed in an outer collar receptacle in the outer collar portion.

In another exemplary embodiment, a needle safety system for a syringe is disclosed. The needle safety system may include a sleeve, within which a barrel of a syringe is moveable, at least partially enclosing a needle of a syringe, and a collar disposed in the sleeve. The collar may have an inner collar portion fixedly attachable to a hub of a syringe, the inner collar portion having a generally cylindrically-shaped base with an inner-collar bore therethrough, an outer collar portion attached to the sleeve and rotatably attached to the inner collar portion, the outer collar portion being of unitary construction and having at least one region which has a radially expandable and automatically compressible section. This section can be shaped like the bellows of an accordion. The outer collar portion further having an outer collar bore with a radially inwardly-extending outer collar ring. Further, the inner collar portion may define a circular channel configured to receive and retain freely rotatable therein the radially inwardly-extending outer collar ring.

In some embodiments of the needle safety system, a distal end of the inner-collar base forms a radially outwardly-extending, distally-facing annular surface, the inner collar portion further having a plurality of radially-disposed, circumferentially-spaced deflectable members protruding distally from the annular surface, each deflectable member sufficiently compliant to allow passage of a distal end of a hub of a syringe through the inner-collar bore and to fixedly attach the inner collar portion to a radially outwardly facing distal-hub surface of a syringe by a radially inwardly-directed force applied by each flexible finger to a radially outwardly-facing distal-hub surface of a syringe, and the distal end of each deflectable member collectively forms the circular channel.

In some embodiments, the needle safety system includes a first guide pin extending radially outward from the outer collar portion and unitarily formed therewith, the guide pin slideably engaging a first guide track formed in the sleeve, and the sleeve defines a proximal opening having an inner radius and the first guide pin extends radially beyond the inner radius.

In some embodiments, the needle safety system includes a second guide pin extending radially outward from the outer collar portion beyond the inner radius and unitarily formed therewith, the second guide pin slideably engaging a second guide track formed in the sleeve.

In some embodiments of the needle safety system, the accordion region is radially compressible such that the first guide pin is moved radially inward to a position not extending beyond the inner radius.

In some embodiments of the needle safety system, an accordion region is radially expandable to allow passage of a distal end of a hub of a syringe through the inner-collar bore while the outer collar portion is rotatably attached to the inner collar portion.

In some embodiments, the needle safety system includes a first guide pin extending radially outward from the outer collar portion and unitarily formed therewith, the guide pin slideably engaging a first guide track formed in the sleeve, and the sleeve defines a proximal opening having an inner radius and the first guide pin extends radially beyond the inner radius.

In some embodiments, the needle safety system includes a second guide pin extending radially outward from the outer collar portion beyond the inner radius and unitarily formed therewith, the second guide pin slideably engaging a second guide track formed in the sleeve.

In some embodiments of the needle safety system, an accordion region is radially compressible such that the first guide pin is moved radially inward to a position not extending beyond the inner radius.

In another exemplary embodiment, a method for assembling a needle safety system for a syringe is disclosed. The method may include inserting an outer collar portion into a sleeve and attaching the outer collar portion thereto, the outer collar portion being of unitary construction and having at least one accordion region comprising at least one living hinge, the accordion region being radially compressible and expandable, the outer collar portion further having an outer collar bore with a radially inwardly-extending outer collar ring; inserting an inner collar portion into the outer collar portion, the inner collar portion having a generally cylindrically-shaped base with an inner-collar bore therethrough, the inner collar portion defining a circular channel, whereby the circular channel retains freely rotatable therein the radially inwardly-extending outer collar ring; and inserting and fixedly attaching the inner collar portion, with the radially inwardly-extending outer collar ring retained therein, onto the distal end of a hub of a syringe.

In some embodiments, the method includes radially compressing the accordion region and inserting a guide pin, extending radially outward from the outer collar portion and unitarily formed therewith, into a guide track formed in the sleeve and the sleeve defines a proximal opening having an inner radius and before compressing the accordion region, the guide pin extends radially beyond the inner radius.

In some embodiments of the method, a distal end of the inner-collar base forms a radially outwardly-extending, distally-facing annular surface, the inner collar portion further having a plurality of radially-disposed, circumferentially-spaced spring-like members protruding distally from the annular surface. The method may further include radially expanding together, the accordion region and deflectable members, while the inner collar portion, with radially inwardly-extending outer collar ring retained therein, is inserted onto a distal end of a hub of a syringe.

BRIEF DESCRIPTION OF THE DRAWINGS

The foregoing summary, as well as the following detailed description of the various embodiments, will be better understood when read in conjunction with the appended drawings. It should be understood, however, that the disclosure is not limited to the precise arrangements and instrumentalities shown.

In the drawings.

DETAILED DESCRIPTION

Reference will now be made in detail to embodiments, examples of which are illustrated in the accompanying drawings. The terminology used herein is for the purpose of describing particular embodiments only and is not intended to be limiting of the disclosure.

As used in the description of the embodiments and the appended claims, the singular forms "a", "an" and "the" are intended to include the plural forms as well, unless the context clearly indicates otherwise. The words "and/or" as used herein refer to and encompass any and all possible combinations of one or more of the associated listed items. The words "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The words "right," "left," "lower" and "upper" designate directions in the drawings to which reference is made. The words "inwardly" and "outwardly" refer to directions toward and away from, respectively, the geometric center of the needle safety shield, and designated parts thereof. The terminology includes the words noted above, derivatives thereof and words of similar import.

Although the words first, second, etc., are used herein to describe various elements, these elements should not be limited by these words. These words are only used to distinguish one element from another. For example, a first track could be termed a second track, and, similarly, a second track could be termed a first track, without departing from the scope of the present disclosure.

As used herein, the words "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

The following description is directed towards various embodiments of a syringe needle safety system.

Referring to the drawings in detail, where like numerals indicate like elements throughout, there is shown in FIGS. 1-14 embodiments of an integrated passive syringe needle safety system with a torqued compression spring and a multipart collar, generally designated 10, and hereafter referred to as the "needle safety system" 10.

Figure 1:
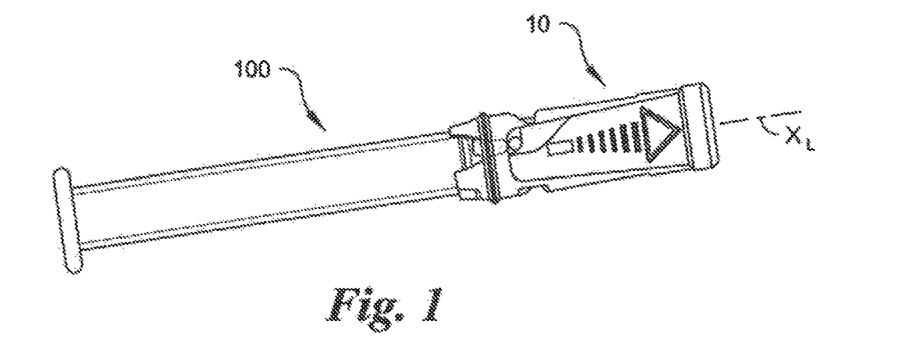
FIG. 1 is a front elevation view of an embodiment of a needle safety system, in accordance with an embodiment, attached to a syringe.

FIG. 1 shows a needle safety system 10 according to some embodiments. The needle safety system 10 is for use with an injection device 100, such as a pharmaceutical syringe. The injection device 100 may be pre-filled with a medicament or may be provided without a medicament for filling by a user.

Figure 2:
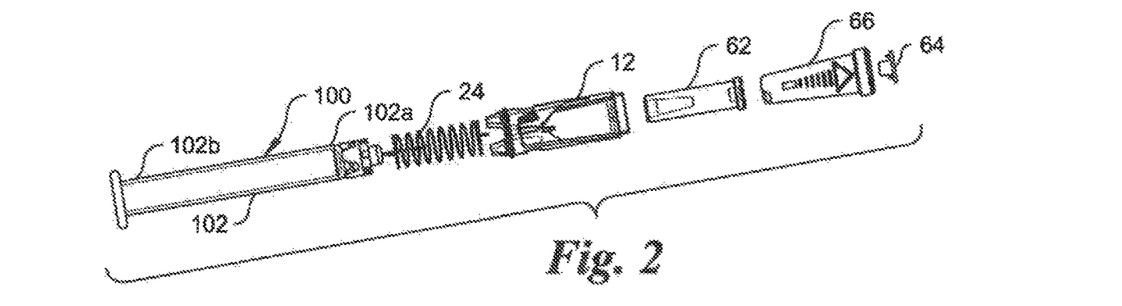
FIG. 2 is an exploded view of the syringe, the needle safety system of FIG. 1, a needle shield and a cap.
Figure 3:
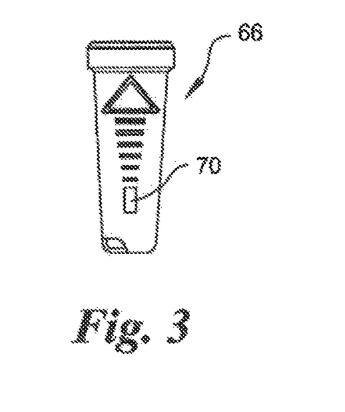
FIG. 3 is a front elevation view of the cap of FIG. 1.
Figure 4:
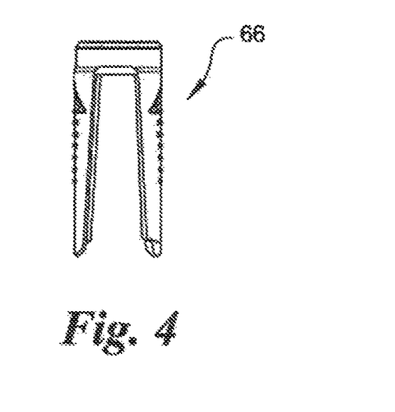
FIG. 4 is a right side elevation view of the cap of FIG. 3.
Figure 5:
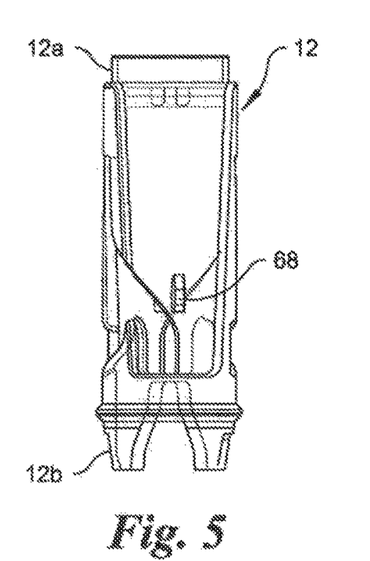
FIG. 5 is a front elevation view of a sleeve of the needle safety system of FIG. 1.

In some embodiments, the injection device 100 has a generally cylindrical barrel 102 extending along a longitudinal axis $X_L$. As shown in FIG. 2, the barrel 102 has a distal end 102a and an opposing proximal end 102b. The barrel 102 may be formed of nearly any material capable of safely enclosing medicaments, including for example, glass or a polymeric material. The distal end 102a of the barrel 102 has a barrel shoulder 104 (FIGS. 12, 13) from which a hub 106 extends (FIG. 13). The hub 106 has a radially outwardly-extending, proximally-facing distal-hub annular shoulder 108 spaced from the barrel shoulder 104 and a radially outwardly-facing distal-hub surface 110 between the barrel shoulder 104 and the distal-hub annular shoulder 108.

A needle 112 (FIG. 13) extends distally from the hub 106 and is in fluid communication with a bore of the barrel 102. The needle 112 may be removably attached to the hub 106. Alternatively, needle 112 may be fixedly attached thereto.

A piston (not shown) slidably receivable in the bore of the barrel 102 is attached to a piston rod (not shown) having a free proximal end that extends from the proximal end 102b of the barrel 102.

As shown in FIG. 2, the needle safety system 10 has a sleeve 12, within which the barrel 102 is moveable, at least partially enclosing the needle 112. In some embodiments, the sleeve 12 may be fabricated from a polymeric material as two molded first and second semi-cylindrical piece parts, each being a mirror image of the other, subsequently fused together to form the single unitary sleeve 12. The sleeve 12 has a distal end 12a, a proximal end 12b (FIG. 5) and is movable relative to the barrel 102 along the longitudinal axis "$X_L$" in a distal, extended direction and in a proximal, retracted direction opposite the distal direction as further discussed below.

Figure 6:
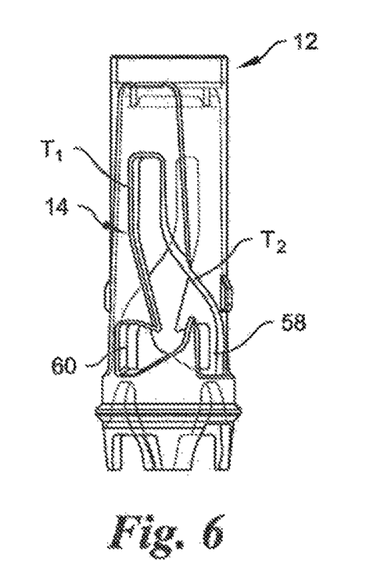
FIG. 6 is a right side elevation view of the sleeve of FIG. 5.

FIG. 6 shows guide tracks 14 formed in the sleeve 12. In some embodiments, a pair of guide tracks 14 are formed in the inner surface of the sleeve 12. Each guide track 14 may be formed in opposite sides of sleeve 12 (i.e., diametrically opposed), for example. The guide track 14 has a first track segment $T_1$ beginning with a first catch 58 and a second track segment $T_2$ contiguous with the first track segment $T_1$ and ending with a second catch 60.

Figure 11:
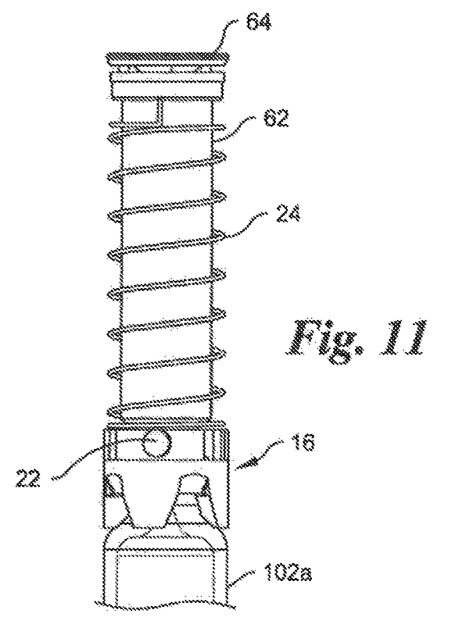
FIG. 11 is a front elevation view of the needle safety system of FIG. 9 with the sleeve thereof removed and the cap removed.
Figure 12:
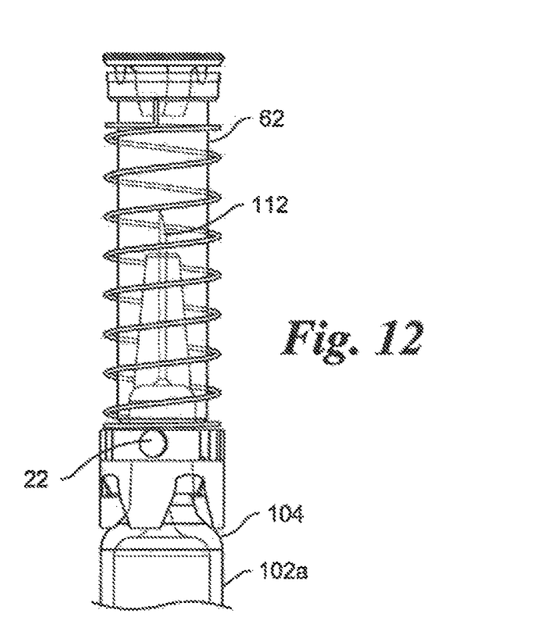
FIG. 12 is a front elevation view of the needle safety system of FIG. 9 with the sleeve thereof removed, the cap removed and the needle shield shown in transparency.
Figure 13:
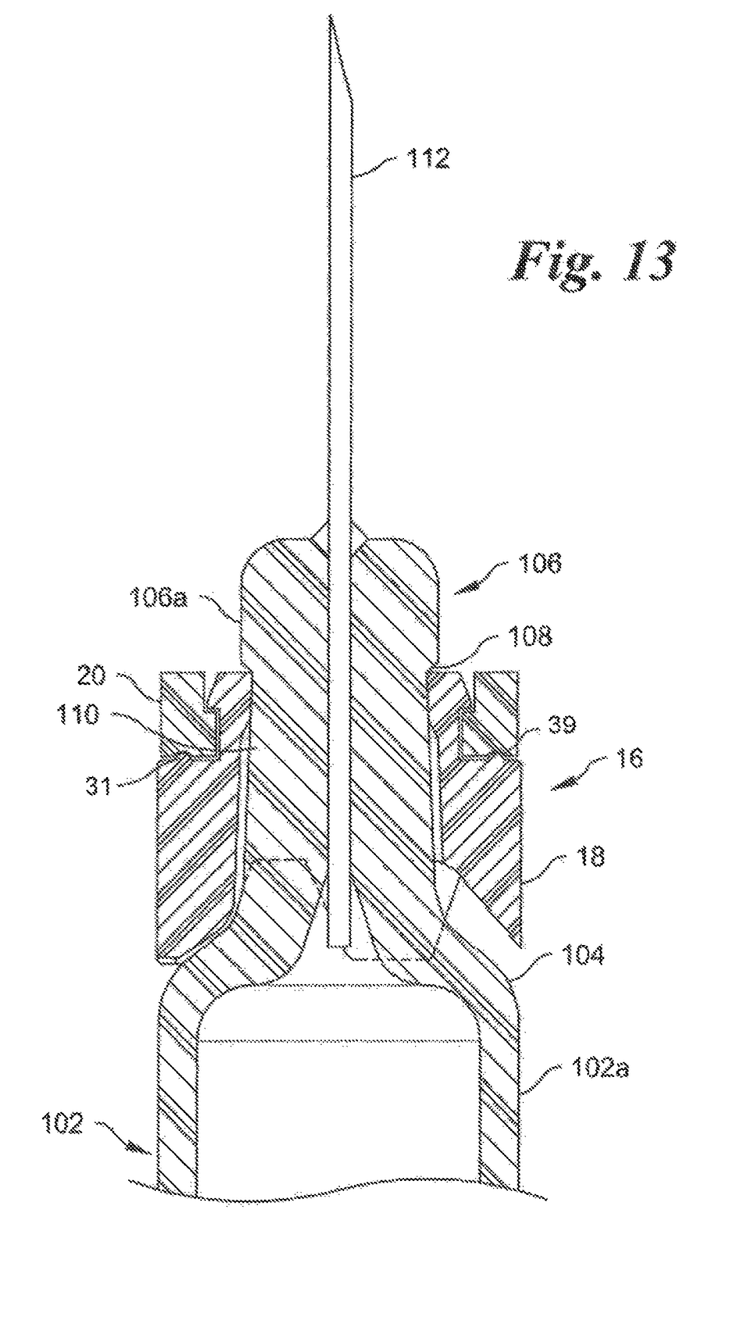
FIG. 13 is a cross sectional view of the collar of the needle safety system mounted on the distal portion of the syringe of FIG. 1.

FIGS. 11-13 show a multi-part collar 16 disposed in the sleeve 12. In one embodiment, the multi-part collar 16 includes an inner collar 18 fixedly connectable to the hub 106 and an outer collar 20 rotatably attached to the inner collar 18 about a rotational axis, but the multi-part collar 16 may include additional collars. A guide pin 22 extending radially outwardly from the outer collar 20 slideably engages the guide track 14. In some embodiments, a pair of guide pins 22 engage corresponding guide tracks 14 in the sleeve 12. In some embodiments more than two collars may be used.

The outer collar 20, including guide pins 22, may be composed of a polymeric or metallic material, for example, a rigid polymer such as acrylic butyl styrene. Moreover, the outer collar 20, including guide pins 22, may be of unitary, i.e., monolithic, construction. The outer collar 20 may include one or more regions 23 which have at least one radially expandable and automatically compressible section. This region/section can be shaped like a bellows of an accordion or could have a spring-like shape. The at least one section 23 extends circumferentially and has a plurality of thin walls with memory, which snake back and forth circumferentially around the outer collar 20. The thin walls may pivot and/or flex as living hinges and collectively deform to permit the accordion regions 23 to act as a spring, i.e., compress or expand in a direction other than the direction of the rotational axis and/or pivot away from or toward the rotational axis. In an embodiment, the outer collar 20 has two diametrically opposed accordion regions 23, which permit the guide pins 22 to move at least radially toward and away from one another. During assembly, compression may be applied to the outer collar 20 moving the guide pins 22 toward one another to allow them to be positioned at and engage the corresponding guide tracks 14. For example, the sleeve 12 may define a proximal opening having an inner radius less than the length of each of the guide pins 22 extending from the outer collar 20 while the outer collar 20 is uncompressed. During compression, the guide pins 22 are moved to a position where they do not extend beyond the inner radius to allow them to be inserted into the sleeve 12. After the guide pins 22 have engaged the corresponding guide tracks 14, the applied compression may be removed, causing the accordion regions 23 and the guide pins 22 to return or substantially return to their previously uncompressed positions.

Figure 7:
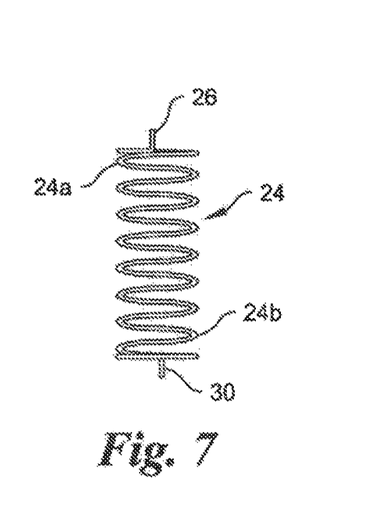
FIG. 7 is an enlarged view of a torqueable compression spring of the needle safety system of FIG. 1.
Figure 8:
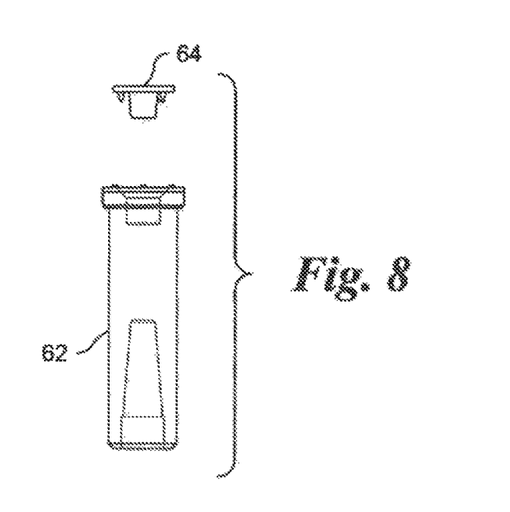
FIG. 8 is an enlarged view of the needle shield and closure of FIG. 2.
Figure 9:
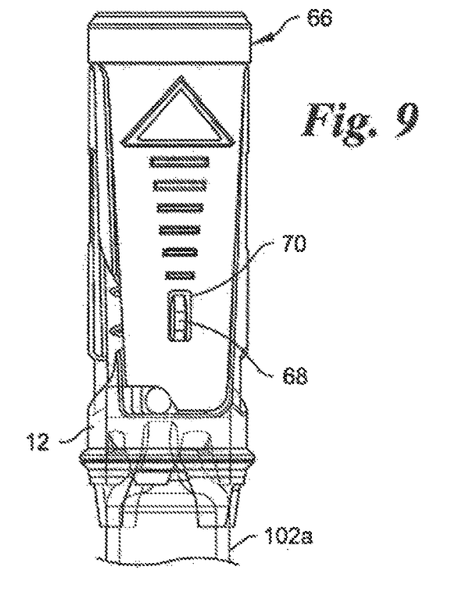
FIG. 9 is a front elevation view of the needle safety system of FIG. 1, engaged with a syringe, needle shield and cap.
Figure 10:
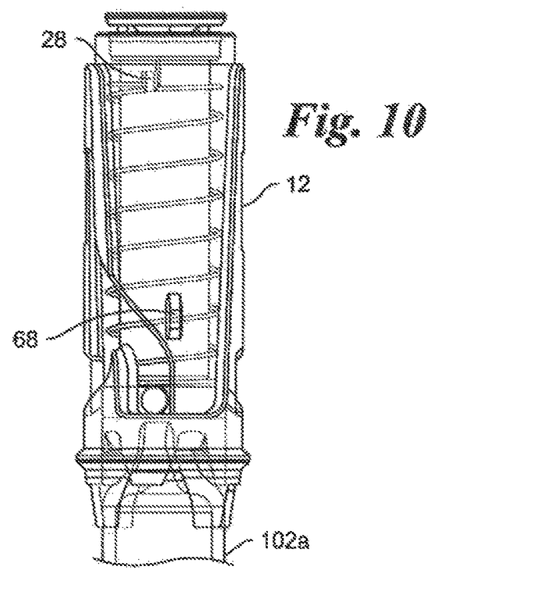
FIG. 10 is a front elevation view of the needle safety system of FIG. 9 with the cap removed.

A torqueable compression spring 24 extends between the outer collar 20 and the sleeve 12. FIG. 7 illustrates the compression spring 24 according to an embodiment. The torqueable compression spring 24 biases the sleeve 12 in a distal direction and also biases the outer collar 20 in rotation relative to the sleeve 12. In some embodiments, the torqueable compression spring 24 has a distal end 24a with a distally-extending leg 26 disposed in a sleeve receptacle 28 (FIG. 10) in the distal end 12a of the sleeve 12 and a proximal end 24b with a proximally-extending leg 30 disposed in an outer collar receptacle 32 (FIG. 14) in the outer collar 20. In an embodiment, a pair of diametrically opposed outer collar receptacles 32 are formed in the outer collar 20, either one of which may receive the proximally-extending leg 30. By having two outer collar receptacles 32 configured to receive the proximally-extending leg 30, ease of assembly may be improved and assembly time may be otherwise reduced.

Figure 14:
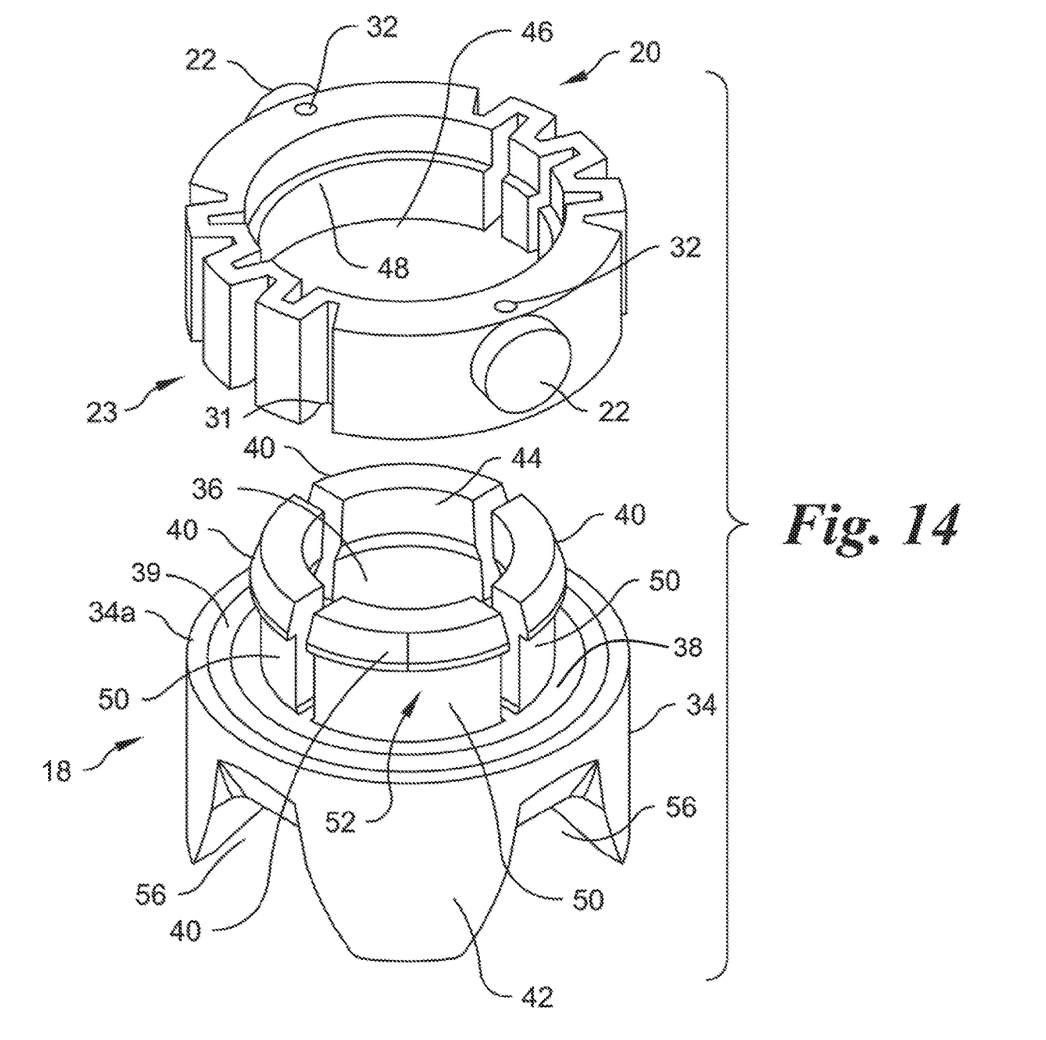
FIG. 14 is an exploded perspective view of an embodiment of a multipart collar for the needle safety system of FIG. 1.

FIGS. 13 and 14 show the inner collar 18 and the outer collar 20. The inner collar 18 has a generally cylindrically-shaped base 34 with an inner-collar bore 36 therethrough. A distal end 34a of the inner-collar base 34 forms a radially outwardly-extending, distally-facing annular surface 38. A plurality of radially-disposed, circumferentially-spaced elastically deflectable, i.e., expandable and contractible, members 40 protrude distally from the annular surface 38. In addition, a half-toroidal ring 39 extends distally from the annular surface 38 at a radially outer position with respect to the deflectable members 40. A channel 50 formed in the distal end of each deflectable member 40 collectively forms a circular channel 52 circumscribing deflectable members 40. Each deflectable member 40 is sufficiently compliant to allow passage of the distal end 106a of the hub 106 through the inner-collar bore 36 and to fixedly attach the inner collar 18 to the radially outwardly-facing distal-hub surface 110 by a radially inwardly-directed force applied by each deflectable member 40 to the radially outwardly-facing distal-hub surface 110. A plurality of radially-disposed, circumferentially-spaced-apart legs 42 protrude proximally from the inner collar base 34. When the inner collar 18 is fixedly attached to the hub 106, the distal end of each deflectable member 40 abuts the proximally-facing distal-hub annular shoulder 108 and a proximal end of each circumferentially-spaced-apart leg 42 abuts the barrel shoulder 104.

In some embodiments of the inner collar 18, at least one cut-out 56 is provided between the circumferentially-spaced-apart legs 42 allowing inspection of contents inside the barrel 102.

In some embodiments of the injection device 100, the radially outwardly-facing distal-hub surface 110 has a taper. For such embodiments, the opposed radially inwardly-facing surface 44 of the distal end of each deflectable member 40 may have a corresponding taper.

The outer collar 20 has an outer collar bore 46 with a radially inwardly-extending outer collar ring 48 that is received and freely rotatably retained in the circular channel 52 circumscribing the deflectable members 40. In an embodiment, the axial height of the outer collar ring 48 is less than the axial height defined by the inside of the circular channel 52. The proximal surface of the outer collar 20 defines an arc-shaped channel 31 sufficiently sized to receive the half-toroidal ring 39 from inner collar 18 when the outer collar 20 is attached to the inner collar 18. In an embodiment, the radius of curvature of the arc-shaped channel 31 is larger than the radius of curvature for the half-toroidal ring 39.

The outer collar 20 is sufficiently compliant and sized to allow passage of the deflectable members 40 through the outer collar bore 46 and insertion of the outer collar ring 48 in the circular channel 52 and to return to an initial outer collar configuration in which the outer collar 20 is freely rotatable in only one degree of freedom relative to the inner collar 18. The outer collar 20 may be attached to the sleeve 12 before the outer collar 20 is attached to the inner collar 18. Thus, the outer collar 20 and the sleeve 12 may be positioned together onto the inner collar 18. After the outer collar 20 has been attached to the inner collar 18, the accordion regions 23 may help permit the deflectable members 40 to flex or expand radially outward when the hub 106 passes through the inner collar bore 36. Thus, as a single subassembly, the safety system 10 may be assembled onto the injection device 100.

FIG. 6 shows the sleeve 12 with guide tracks 14. When the inner collar 18 is attached to the hub 106 and the guide pin 22 extending radially outwardly from the outer collar 20 is positioned in the first catch 58 of the first track segment $T_1$, the needle safety system 10 is in a pre-injection position in which the needle 112 is at least partially enclosed in the sleeve 12. When the guide pin 22 is moved out of the first catch 58 to the distal end 12a of the first track segment $T_1$, the needle safety system 10 is in a full-insertion position exposing the needle 112. When the guide pin 22 is moved along the second track segment $T_2$ to the second catch 60, the needle 112 is entirely enclosed in the sleeve 12 and the guide pin 22 is locked in the second catch 60 by the rotational bias of the torqueable compression spring 24 toward the second catch 60.

FIGS. 11 and 12 show the needle safety system 10 engaged with a syringe 100 with the sleeve 12 of the needle safety system 10 removed. A generally cylindrical removable needle shield 62 may be used with the needle safety system 10 to protect the needle 112. The needle shield 62 may be rigid or comprised of rubber and is inserted over the needle 112 through the opening of the cap 66 and is usually covered with a button or closure 64 at the distal end of the needle shield 62 and cap 66. The needle shield 62 is configured and sized to fit in the sleeve 12 and in the base of the cap 66 and also is attached to the cap 66. The cap 66 is releasably retained by a radially outwardly extending protrusion 68 in the sleeve 12 insertable in a slot 70 in the cap 66. Prior to an injection, the needle shield 62 may be removed from the needle 112 by grasping the cap 66 and removing the cap 66 thereby removing the needle shield 62.

In some embodiments, the assembled needle safety system 10 is assembled with an injection device 100, e.g., a syringe, by aligning both concentrically and applying a compression force in a linear direction to the system 10 and the syringe 100 together. The compression force may be applied by a force to at least one of the closure 64 and the flange of the syringe 100. The assembled needle safety system 10 and syringe 100 may then be packaged into nesting trays (not shown), e.g., one-hundred per tray. The nesting trays, having the respective assembled needle safety systems 10 and syringes 100 loaded therein, may then be delivered to an automatic syringe filling system having the filling lines, wherein a substance, e.g., a medicament, drug or other injectable medicine, is filled in the syringes 100 and respective plungers (not shown) are inserted into the syringes 100. Alternatively, the assembled needle safety systems 10 may be inserted in the nesting trays the nesting trays with the needle safety systems 100 loaded therein delivered to the automatic syringe filling system. Syringes 100 may then be assembled to the needle safety systems 10, respectively, held in the nesting trays. The syringes 100 may then be filled with the substance and the plungers thereafter inserted into the syringes 100.

The foregoing detailed description of the disclosure has been disclosed with reference to specific embodiments. However, the disclosure is not intended to be exhaustive or to limit the disclosure to the precise forms disclosed. Those skilled in the art will appreciate that changes could be made to the embodiments described above without departing from the broad inventive concept thereof. Therefore, the disclosure is intended to cover modifications within the spirit and scope of the present disclosure as defined by the appended claims.

We claim:

1. A needle safety system for a syringe, the needle safety system comprising:
    a sleeve configured to partially enclose a needle of the syringe;
    a guide track formed in the sleeve; and
    a collar disposed in the sleeve, the collar comprising:
        an inner collar portion configured to fixedly attach to a hub of the syringe, the inner collar portion having a generally cylindrically-shaped base with an inner-collar bore therethrough;
        an outer collar portion rotatably attached to the inner collar portion, the outer collar portion being of unitary construction and having at least one accordion region which is radially compressible and expandable, the outer collar portion further having an outer collar bore with a radially inwardly-extending outer collar ring; and
        at least one guide pin extending radially from the outer collar portion, the at least one guide pin configured to slide within the guide track; and
    a spring extending between the outer collar portion and the sleeve, the spring biasing the sleeve in a distal direction and also biasing the outer collar portion in rotation relative to the sleeve,
    wherein the inner collar portion defines a circular channel configured to receive and retain freely rotatable therein the radially inwardly-extending outer collar ring.

2. The needle safety system according to claim 1, wherein the inner collar portion comprises:
    a radially outwardly-extending, distally-facing annular surface at a distal end of the base of the inner collar portion;
    a plurality of radially-disposed, circumferentially-spaced, and compliant deflectable members protruding distally from the annular surface, each deflectable member configured to allow passage of a distal end of the hub of the syringe through the inner-collar bore and to apply a radially inwardly-directed force to a radially outwardly facing distal-hub surface of the syringe, thereby fixedly attaching the inner collar portion to the radially outwardly facing distal-hub surface of the syringe; and
    a plurality of radially-disposed, circumferentially-spaced-apart legs protruding proximally,
    wherein a distal end of each deflectable member abuts a proximally-facing distal-hub annular shoulder of the syringe and a proximal end of each circumferentially-spaced-apart leg abuts a barrel shoulder of the syringe when the inner collar portion is fixedly attached to the hub of the syringe.

3. The needle safety system according to claim 2, wherein at least one cut-out is provided between the circumferentially-spaced-apart legs allowing inspection of contents inside a barrel of the syringe.

4. The needle safety system according to claim 3, wherein an opposed radially inwardly-facing surface of the distal end of each deflectable member has a taper corresponding to the radially outwardly-facing distal-hub surface of a syringe.

5. The needle safety system according to claim 2, wherein a channel formed in the distal end of each deflectable member collectively forms the circular channel in a radially outwardly-facing surface of the inner collar portion.

6. The needle safety system according to claim 5, wherein the outer collar portion is sufficiently compliant and sized to allow passage of the deflectable members through the outer collar bore, and insertion of the outer collar ring in the circular channel and to return to an initial outer collar configuration in which the outer collar portion is freely rotatable in only one degree of freedom relative to the inner collar portion.

7. The needle safety system according to claim 1, wherein the guide track has a first track segment beginning with a first catch, and a second track segment contiguous with the first track segment and ending with a second catch, and
    when the inner collar portion is attached to the hub of the syringe, and the at least one guide pin is positioned in the first catch, the needle safety system is in a pre-injection position,
    when the guide pin is moved out of the first catch to a distal end of the first track segment, the needle safety system is in a full-insertion position exposing the needle of the syringe, and
    when the at least one guide pin is moved along the second track segment to the second catch the needle of the syringe is entirely enclosed in the sleeve and the at least one guide pin is locked in the second catch by the rotational bias of the spring toward the second catch.

8. The needle safety system according to claim 1, wherein the spring has a distal end with a distally extending leg disposed in a sleeve receptacle in a distal end of the sleeve and a proximal end with a proximally extending leg disposed in an outer collar receptacle in the outer collar portion.

9. The needle safety system according to claim 1, wherein a distal end of the base of the inner-collar portion forms a radially outwardly-extending, distally-facing annular surface, the inner collar portion further having a plurality of radially-disposed, circumferentially-spaced deflectable members protruding distally from the annular surface, each deflectable member sufficiently compliant to allow passage of a distal end of the hub of the syringe through the inner-collar bore and to fixedly attach the inner collar portion to a radially outwardly facing distal-hub surface of the syringe by a radially inwardly-directed force applied by each deflectable member to the radially outwardly-facing distal-hub surface of the syringe; and wherein a distal end of each deflectable member collectively forms the circular channel.

10. The needle safety system according to claim 9, wherein the at least one accordion region is radially expandable to allow passage of the distal end of the hub of the syringe through the inner-collar bore while the outer collar portion is rotatably attached to the inner collar portion.

11. The needle safety system according to claim 10, wherein the at least one guide pin comprises a first guide pin extending radially outward from the outer collar portion and unitarily formed therewith, the first guide pin slideably engaging a first guide track formed in the sleeve;

wherein the sleeve defines a proximal opening having an inner radius and the first guide pin extends radially beyond the inner radius.

12. The needle safety system according to claim 11, wherein the at least one guide pin comprises a second guide pin extending radially outward from the outer collar portion beyond the inner radius and unitarily formed therewith, the second guide pin slideably engaging a second guide track formed in the sleeve.

13. The needle safety system according to claim 11, wherein the at least one accordion region is radially compressible such that the first guide pin is configured to be moved radially inward to a position not extending beyond the inner radius.

14. The needle safety system according to claim 1, wherein the at least one guide pin comprises a first guide pin extending radially outward from the outer collar portion and unitarily formed therewith, the first guide pin configured to slide within a first guide track formed in the sleeve;

wherein the sleeve defines a proximal opening having an inner radius and the first guide pin extends radially beyond the inner radius.

15. The needle safety system according to claim 14, wherein the at least one guide pin comprises a second guide pin extending radially outward from the outer collar portion beyond the inner radius and unitarily formed therewith, the second guide pin slideably engaging a second guide track formed in the sleeve.

16. The needle safety system according to claim 14, wherein the at least one accordion region is radially compressible such that the first guide pin is configured to be moved radially inward to a position not extending beyond the inner radius.

17. A syringe assembly comprising the needle safety system of claim 1 and the syringe.

18. A method of assembling the syringe assembly according to claim 17, the method comprising:

placing the needle safety system in a nesting tray;

placing the nesting tray with the needle safety system into an automatic syringe filling system;

inserting the syringe into the needle safety system held in the nesting tray.

19. The method of assembling the syringe assembly according to claim 18, further comprising:

filling the syringe held in the nesting tray with an injectable medicine; and inserting a plunger with a plunger rod into the syringe.

20. A method of assembling a needle safety system for a syringe, the method comprising:

inserting an outer collar portion of unitary constructions and having at least one accordion region, which is radially compressible and expandable, into a sleeve and attaching the outer collar portion thereto by radially compressing the at least one accordion region and inserting a guide pin, extending radially outward from the outer collar portion and unitarily formed therewith, into a guide track formed in the sleeve, the outer collar portion further having an outer collar bore with a radially inwardly-extending outer collar ring;

inserting an inner collar portion into the outer collar portion, the inner collar portion having a generally cylindrically-shaped base with an inner-collar bore therethrough, the inner collar portion defining a circular channel, whereby the circular channel retains freely rotatable therein the radially inwardly-extending outer collar ring; and inserting and fixedly attaching the inner collar portion, with the radially inwardly-extending outer collar ring retained therein, onto a distal end of a hub of the syringe.

21. The method according to claim 20, wherein a distal end of the base of the inner-collar portion forms a radially outwardly-extending, distally-facing annular surface, the inner collar portion further having a plurality of radially-disposed, circumferentially-spaced deflectable members protruding distally from the annular surface; and radially expanding together, the at least one accordion region and deflectable members, while the inner collar portion, with radially inwardly-extending outer collar ring retained therein, is inserted onto the distal end of the hub of the syringe.

* * * * *